United States Patent
Fortune

(10) Patent No.: US 11,125,679 B2
(45) Date of Patent: Sep. 21, 2021

(54) METHOD AND APPARATUS FOR ANALYSING A COMPONENT

(71) Applicant: ROLLS-ROYCE plc, London (GB)

(72) Inventor: James R. Fortune, Derby (GB)

(73) Assignee: ROLLS-ROYCE PLC, London (GB)

(*) Notice: Subject to any disclaimer, the term of this patent is extended or adjusted under 35 U.S.C. 154(b) by 0 days.

(21) Appl. No.: 16/929,144

(22) Filed: Jul. 15, 2020

(65) Prior Publication Data
US 2021/0048384 A1 Feb. 18, 2021

(30) Foreign Application Priority Data
Aug. 16, 2019 (GB) ..................................... 1911749

(51) Int. Cl.
*G01N 21/21* (2006.01)
*G01J 4/04* (2006.01)
(Continued)

(52) U.S. Cl.
CPC ........... *G01N 21/21* (2013.01); *F01D 21/003* (2013.01); *G01J 4/04* (2013.01); *G01N 21/8806* (2013.01);
(Continued)

(58) Field of Classification Search
CPC .... F01D 21/003; G01N 33/20; G01N 33/204; G01N 33/2045; G01N 21/21;
(Continued)

(56) References Cited

U.S. PATENT DOCUMENTS

| 5,426,506 A * | 6/1995 | Ellingson ............... G01N 21/88 250/225 |
| 7,034,931 B2 * | 4/2006 | Jones .................. G01N 21/4788 356/237.2 |

(Continued)

FOREIGN PATENT DOCUMENTS

| EP | 1494275 | 1/2005 |
| EP | 2846155 A1 | 3/2015 |

(Continued)

OTHER PUBLICATIONS

Great Britain search report dated Feb. 6, 2020, issued in GB Patent Application No. 1911749.8.
(Continued)

*Primary Examiner* — Gordon J Stock, Jr.

(57) ABSTRACT

A method of analysing a component formed from a metal alloy to identify a possible defect, wherein the metal alloy comprises a first crystal grain region and the possible defect comprises a second crystal grain region aligned to a different axis to the first crystal grain region, the method comprising the steps of: obtaining a first image of the component illuminated using a first polarisation state of light, the first image comprising first polarisation data; obtaining a second image of the component illuminated using a second polarisation state of light different to the first polarisation state, the second image comprising second polarisation data; determining a difference in polarisation data for plural pixels of the first image between each pixel of the first image and a corresponding pixel of the second image; and identifying pixels corresponding to the second crystal grain region based on the difference in polarisation data.

20 Claims, 5 Drawing Sheets

(51) Int. Cl.
*G01N 33/2045* (2019.01)
*F01D 21/00* (2006.01)
*G01N 21/95* (2006.01)
*G01N 21/88* (2006.01)
*G01N 21/84* (2006.01)

(52) U.S. Cl.
CPC ..... *G01N 21/9515* (2013.01); *G01N 33/2045* (2019.01); *G01N 2021/216* (2013.01); *G01N 2021/8477* (2013.01); *G01N 2021/8848* (2013.01); *G01N 2223/646* (2013.01)

(58) Field of Classification Search
CPC ...... G01N 21/211; G01N 21/23; G01N 21/47; G01N 21/4738; G01N 21/55; G01N 21/84; G01N 21/85; G01N 21/8806; G01N 21/95; G01N 21/9501; G01N 21/9505; G01N 21/9515; G01N 21/9506; G01N 21/95607; G01N 21/95684; G01N 2021/216; G01N 2021/217; G01N 2021/218; G01N 2021/4733; G01N 2021/4763; G01N 2021/4792; G01N 2021/8427; G01N 2021/8438; G01N 2021/8477; G01N 2021/8848; G01N 2021/8887; G01N 2223/60; G01N 2223/646; G01N 2223/6462; G01B 11/16; G01B 11/168; G01B 11/26; G01B 11/27; G01B 11/272; G01B 11/30; G01B 11/303; G01B 11/306; G01J 4/04

See application file for complete search history.

(56) References Cited

U.S. PATENT DOCUMENTS

| | | | |
|---|---|---|---|
| 10,215,710 B2* | 2/2019 | Wingfield | G01N 21/8806 |
| 2003/0112447 A1 | 6/2003 | Harding et al. | |
| 2014/0176698 A1* | 6/2014 | Banerjee | G01N 21/21 |
| | | | 348/92 |
| 2020/0271911 A1* | 8/2020 | Hoover | G01N 21/21 |

FOREIGN PATENT DOCUMENTS

| | | |
|---|---|---|
| EP | 2846156 A1 | 3/2015 |
| EP | 3156783 A2 | 4/2017 |
| JP | H04102049 | 4/1992 |
| JP | H0566381 | 3/1993 |
| JP | H05180775 | 7/1993 |

OTHER PUBLICATIONS

European search report dated Dec. 2, 2020, issued in EP Patent Application No. 20187412.0.

* cited by examiner

METHOD AND APPARATUS FOR ANALYSING A COMPONENT

CROSS-REFERENCE TO RELATED APPLICATIONS

This specification is based upon and claims the benefit of priority from UK Patent Application Number GB 1911749.8 filed on 16 Aug. 2019, the entire contents of which are incorporated herein by reference.

BACKGROUND

Technical Field

The present disclosure relates to visual analysis of components, for example components formed from a metal alloy, to identify potential defects in such components. The present disclosure provides an apparatus and methods as set out in the appended claims.

Description of Related Art

Coded photography is a process that may be used to assist in the analysis of fabricated components. In a coded photography process, a number of images of an object are taken in succession, with one parameter being changed between images and the other parameters being held constant. One example of a parameter that may be changed between the images is the angle of illumination of the light used to illuminate the object.

Successive images (i.e. an image stack) can be obtained using various parameters and the greyscale value of the pixels of the images within the image stack can be used to give information regarding the geometry or other properties of the object being imaged.

Analysis of this image data can be used to identify defects, improving the manufacturing process of the components and helping to identify any components not suitable for use. However, the identification of certain defects in components can still prove difficult. It would therefore be desirable to provide an improved method for visual analysis of components.

SUMMARY

According to a first aspect there is provided a method of analysing a component, formed from a metal alloy, to identify a possible defect, wherein the metal alloy comprises a first crystal grain region and the possible defect comprises a second crystal grain region aligned to a different axis to the first crystal grain region, the method comprising the steps of: obtaining a first image of the component illuminated using a multi-pixel sensor and a first polarisation state of light, the first image comprising first polarisation data; obtaining a second image of the component illuminated using a multi-pixel sensor and a second polarisation state of light different to the first polarisation state, the second image comprising second polarisation data; determining a difference in polarisation for plural pixels of the first image between each pixel of the first image and a corresponding pixel of the second image; and identifying pixels corresponding to the second crystal grain region based on the difference in polarisation.

Each pixel may be categorised as corresponding to the first crystal grain region by identifying a first region of the differences in polarisation in a first range or corresponding to the second crystal grain region by identifying a second region of the differences in polarisation in a second range, where the first range is different to the second range.

Each pixel may be categorised as corresponding to the second crystal grain region if the difference in polarisation exceeds a threshold value.

The method may further comprise determining the angle of orientation of the second crystal grain region relative to the angle of orientation of the first crystal grain region based on the difference in polarisation.

The method may further comprise determining the location of the boundary between the second crystal grain region and the first crystal grain region based on the difference in polarisation.

The method may further comprise determining the area of the second crystal grain region based on the difference in polarisation.

The component may be illuminated using the first polarisation state of light at the same perspective and orientation relative to the illumination using the second polarisation stage of light.

The second image may be obtained at the same perspective and orientation relative to the component as the first image.

At least one of the first and second polarisation states may be a linear polarisation state.

Both of the first and second polarisation states may be a linear polarisation state and the first linear polarisation state is at a different polarisation angle with respect to the plane of incidence to the second linear polarisation state.

At least one of the first and second polarisation states may be a circular polarisation state.

Each of the first image and the second image may further comprise intensity data; and the method may further comprise the step of determining a difference in intensity for plural pixels of the first image between each pixel of the first image and a corresponding pixel of the second image; wherein the identification of pixels corresponding to the second crystal grain region is additionally based on the difference in intensity.

The method may further comprise obtaining a plurality of further images of the component wherein each of the further plurality of images is obtained using a different polarisation state to each of the other of the further plurality of images; and storing the polarisation data of each of the images of the component in a matrix of image data; wherein the identification of pixels corresponding to the second crystal grain region may be performed by analysis of the matrix of image data.

According to a second aspect there is provided a method of analysing a component formed from a metal alloy to identify a possible defect, wherein the metal alloy comprises a first crystal grain region and the possible defect comprises a second crystal grain region aligned to a different axis to the first crystal grain region; and the method comprises the steps of: obtaining an image of the component illuminated using a first polarisation state of light, the first image comprising polarisation data; determining a difference in polarisation for plural pixels of the first image between each pixel of the first image and at least one other pixel of the first image; and identifying pixels corresponding to the second crystal grain region based on the difference in polarisation.

The component may a component of a gas turbine engine. The component may optionally be a turbine blade.

According to a third aspect there is provided apparatus for analysing a component formed from a metal alloy, the apparatus comprising: a light source configured to produce polarised light; a detector comprising a sensor with multiple pixels, each pixel configured to detect the polarisation state of light incident on the pixel; and an analyser; wherein the apparatus is configured to perform the method of the first aspect.

As noted elsewhere herein, the present disclosure may relate to a gas turbine engine. Such a gas turbine engine may comprise an engine core comprising a turbine, a combustor, a compressor, and a core shaft connecting the turbine to the compressor. Such a gas turbine engine may comprise a fan (having fan blades) located upstream of the engine core.

Arrangements of the present disclosure may be particularly, although not exclusively, beneficial for fans that are driven via a gearbox. Accordingly, the gas turbine engine may comprise a gearbox that receives an input from the core shaft and outputs drive to the fan so as to drive the fan at a lower rotational speed than the core shaft. The input to the gearbox may be directly from the core shaft, or indirectly from the core shaft, for example via a spur shaft and/or gear. The core shaft may rigidly connect the turbine and the compressor, such that the turbine and compressor rotate at the same speed (with the fan rotating at a lower speed).

The gas turbine engine as described and/or claimed herein may have any suitable general architecture. For example, the gas turbine engine may have any desired number of shafts that connect turbines and compressors, for example one, two or three shafts. Purely by way of example, the turbine connected to the core shaft may be a first turbine, the compressor connected to the core shaft may be a first compressor, and the core shaft may be a first core shaft. The engine core may further comprise a second turbine, a second compressor, and a second core shaft connecting the second turbine to the second compressor. The second turbine, second compressor, and second core shaft may be arranged to rotate at a higher rotational speed than the first core shaft.

In such an arrangement, the second compressor may be positioned axially downstream of the first compressor. The second compressor may be arranged to receive (for example directly receive, for example via a generally annular duct) flow from the first compressor.

The gearbox may be arranged to be driven by the core shaft that is configured to rotate (for example in use) at the lowest rotational speed (for example the first core shaft in the example above). For example, the gearbox may be arranged to be driven only by the core shaft that is configured to rotate (for example in use) at the lowest rotational speed (for example only be the first core shaft, and not the second core shaft, in the example above). Alternatively, the gearbox may be arranged to be driven by any one or more shafts, for example the first and/or second shafts in the example above.

The gearbox may be a reduction gearbox (in that the output to the fan is a lower rotational rate than the input from the core shaft). Any type of gearbox may be used. For example, the gearbox may be a "planetary" or "star" gearbox, as described in more detail elsewhere herein. The gearbox may have any desired reduction ratio (defined as the rotational speed of the input shaft divided by the rotational speed of the output shaft), for example greater than 2.5, for example in the range of from 3 to 4.2, or 3.2 to 3.8, for example on the order of or at least 3, 3.1, 3.2, 3.3, 3.4, 3.5, 3.6, 3.7, 3.8, 3.9, 4, 4.1 or 4.2. The gear ratio may be, for example, between any two of the values in the previous sentence. Purely by way of example, the gearbox may be a "star" gearbox having a ratio in the range of from 3.1 or 3.2 to 3.8. In some arrangements, the gear ratio may be outside these ranges.

In any gas turbine engine as described and/or claimed herein, a combustor may be provided axially downstream of the fan and compressor(s). For example, the combustor may be directly downstream of (for example at the exit of) the second compressor, where a second compressor is provided. By way of further example, the flow at the exit to the combustor may be provided to the inlet of the second turbine, where a second turbine is provided. The combustor may be provided upstream of the turbine(s).

The or each compressor (for example the first compressor and second compressor as described above) may comprise any number of stages, for example multiple stages. Each stage may comprise a row of rotor blades and a row of stator vanes, which may be variable stator vanes (in that their angle of incidence may be variable). The row of rotor blades and the row of stator vanes may be axially offset from each other.

The or each turbine (for example the first turbine and second turbine as described above) may comprise any number of stages, for example multiple stages. Each stage may comprise a row of rotor blades and a row of stator vanes. The row of rotor blades and the row of stator vanes may be axially offset from each other. Each fan blade may be defined as having a radial span extending from a root (or hub) at a radially inner gas-washed location, or 0% span position, to a tip at a 100% span position. The ratio of the radius of the fan blade at the hub to the radius of the fan blade at the tip may be less than (or on the order of) any of: 0.4, 0.39, 0.38 0.37, 0.36, 0.35, 0.34, 0.33, 0.32, 0.31, 0.3, 0.29, 0.28, 0.27, 0.26, or 0.25. The ratio of the radius of the fan blade at the hub to the radius of the fan blade at the tip may be in an inclusive range bounded by any two of the values in the previous sentence (i.e. the values may form upper or lower bounds), for example in the range of from 0.28 to 0.32. These ratios may commonly be referred to as the hub-to-tip ratio. The radius at the hub and the radius at the tip may both be measured at the leading edge (or axially forwardmost) part of the blade. The hub-to-tip ratio refers, of course, to the gas-washed portion of the fan blade, i.e. the portion radially outside any platform.

The radius of the fan may be measured between the engine centreline and the tip of a fan blade at its leading edge. The fan diameter (which may simply be twice the radius of the fan) may be greater than (or on the order of) any of: 220 cm, 230 cm, 240 cm, 250 cm (around 100 inches), 260 cm, 270 cm (around 105 inches), 280 cm (around 110 inches), 290 cm (around 115 inches), 300 cm (around 120 inches), 310 cm, 320 cm (around 125 inches), 330 cm (around 130 inches), 340 cm (around 135 inches), 350 cm, 360 cm (around 140 inches), 370 cm (around 145 inches), 380 (around 150 inches) cm, 390 cm (around 155 inches), 400 cm, 410 cm (around 160 inches) or 420 cm (around 165 inches). The fan diameter may be in an inclusive range bounded by any two of the values in the previous sentence (i.e. the values may form upper or lower bounds), for example in the range of from 240 cm to 280 cm or 330 cm to 380 cm.

The rotational speed of the fan may vary in use. Generally, the rotational speed is lower for fans with a higher diameter. Purely by way of non-limitative example, the rotational speed of the fan at cruise conditions may be less than 2500 rpm, for example less than 2300 rpm. Purely by way of further non-limitative example, the rotational speed of the fan at cruise conditions for an engine having a fan diameter in the range of from 220 cm to 300 cm (for example 240 cm to 280 cm or 250 cm to 270 cm) may be in the range of from 1700 rpm to 2500 rpm, for example in the range of from 1800 rpm to 2300 rpm, for example in the range of from 1900 rpm to 2100 rpm. Purely by way of further non-limitative example, the rotational speed of the fan at cruise conditions for an engine having a fan diameter in the range of from 330 cm to 380 cm may be in the range of from 1200 rpm to 2000 rpm, for example in the range of from 1300 rpm to 1800 rpm, for example in the range of from 1400 rpm to 1800 rpm.

In use of the gas turbine engine, the fan (with associated fan blades) rotates about a rotational axis. This rotation results in the tip of the fan blade moving with a velocity $U_{tip}$. The work done by the fan blades on the flow results in an enthalpy rise dH of the flow. A fan tip loading may be defined as $dH/U_{tip}^2$, where dH is the enthalpy rise (for example the 1-D average enthalpy rise) across the fan and $U_{tip}$ is the (translational) velocity of the fan tip, for example at the leading edge of the tip (which may be defined as fan tip radius at leading edge multiplied by angular speed). The fan tip loading at cruise conditions may be greater than (or on the order of) any of: 0.28, 0.29, 0.30, 0.31, 0.32, 0.33, 0.34, 0.35, 0.36, 0.37, 0.38, 0.39 or 0.4 (all units in this paragraph being $Jkg^{-1}K^{-1}/(ms^{-1})^2$). The fan tip loading may be in an inclusive range bounded by any two of the values in the previous sentence (i.e. the values may form upper or lower bounds), for example in the range of from 0.28 to 0.31, or 0.29 to 0.3.

Gas turbine engines in accordance with the present disclosure may have any desired bypass ratio, where the bypass ratio is defined as the ratio of the mass flow rate of the flow through the bypass duct to the mass flow rate of the flow through the core at cruise conditions. In some arrangements the bypass ratio may be greater than (or on the order of) any of the following: 10, 10.5, 11, 11.5, 12, 12.5, 13, 13.5, 14, 14.5, 15, 15.5, 16, 16.5, 17, 17.5, 18, 18.5, 19, 19.5 or 20. The bypass ratio may be in an inclusive range bounded by any two of the values in the previous sentence (i.e. the values may form upper or lower bounds), for example in the range of form 12 to 16, 13 to 15, or 13 to 14. The bypass duct may be substantially annular. The bypass duct may be radially outside the engine core. The radially outer surface of the bypass duct may be defined by a nacelle and/or a fan case.

The overall pressure ratio of a gas turbine engine as described and/or claimed herein may be defined as the ratio of the stagnation pressure upstream of the fan to the stagnation pressure at the exit of the highest pressure compressor (before entry into the combustor). By way of non-limitative example, the overall pressure ratio of a gas turbine engine as described and/or claimed herein at cruise may be greater than (or on the order of) any of the following: 35, 40, 45, 50, 55, 60, 65, 70, 75. The overall pressure ratio may be in an inclusive range bounded by any two of the values in the previous sentence (i.e. the values may form upper or lower bounds), for example in the range of from 50 to 70.

Specific thrust of an engine may be defined as the net thrust of the engine divided by the total mass flow through the engine. At cruise conditions, the specific thrust of an engine described and/or claimed herein may be less than (or on the order of) any of the following: 110 $Nkg^{-1}s$, 105 $Nkg^{-1}s$, 100 $Nkg^{-1}s$, 95 $Nkg^{-1}s$, 90 $Nkg^{-1}s$, 85 $Nkg^-s$ or 80 $Nkg^-s$. The specific thrust may be in an inclusive range bounded by any two of the values in the previous sentence (i.e. the values may form upper or lower bounds), for example in the range of from 80 $Nkg^-s$ to 100 $Nkg^{-1}s$, or 85 $Nkg^-s$ to 95 $Nkg^-s$. Such engines may be particularly efficient in comparison with conventional gas turbine engines.

A gas turbine engine as described and/or claimed herein may have any desired maximum thrust. Purely by way of non-limitative example, a gas turbine as described and/or claimed herein may be capable of producing a maximum thrust of at least (or on the order of) any of the following: 160 kN, 170 kN, 180 kN, 190 kN, 200 kN, 250 kN, 300 kN, 350 kN, 400 kN, 450 kN, 500 kN, or 550 kN. The maximum thrust may be in an inclusive range bounded by any two of the values in the previous sentence (i.e. the values may form upper or lower bounds). Purely by way of example, a gas turbine as described and/or claimed herein may be capable of producing a maximum thrust in the range of from 330 kN to 420 kN, for example 350 kN to 400 kN. The thrust referred to above may be the maximum net thrust at standard atmospheric conditions at sea level plus 15 degrees C. (ambient pressure 101.3 kPa, temperature 30 degrees C.), with the engine static.

In use, the temperature of the flow at the entry to the high pressure turbine may be particularly high. This temperature, which may be referred to as TET, may be measured at the exit to the combustor, for example immediately upstream of the first turbine vane, which itself may be referred to as a nozzle guide vane. At cruise, the TET may be at least (or on the order of) any of the following: 1400K, 1450K, 1500K, 1550K, 1600K or 1650K. The TET at cruise may be in an inclusive range bounded by any two of the values in the previous sentence (i.e. the values may form upper or lower bounds). The maximum TET in use of the engine may be, for example, at least (or on the order of) any of the following: 1700K, 1750K, 1800K, 1850K, 1900K, 1950K or 2000K. The maximum TET may be in an inclusive range bounded by any two of the values in the previous sentence (i.e. the values may form upper or lower bounds), for example in the range of from 1800K to 1950K. The maximum TET may occur, for example, at a high thrust condition, for example at a maximum take-off (MTO) condition.

A fan blade and/or aerofoil portion of a fan blade described and/or claimed herein may be manufactured from any suitable material or combination of materials. For example at least a part of the fan blade and/or aerofoil may be manufactured at least in part from a composite, for example a metal matrix composite and/or an organic matrix composite, such as carbon fibre. By way of further example at least a part of the fan blade and/or aerofoil may be manufactured at least in part from a metal, such as a titanium based metal or an aluminium based material (such as an aluminium-lithium alloy) or a steel based material. The fan blade may comprise at least two regions manufactured using different materials. For example, the fan blade may have a protective leading edge, which may be manufactured using a material that is better able to resist impact (for example from birds, ice or other material) than the rest of the blade. Such a leading edge may, for example, be manufactured using titanium or a titanium-based alloy. Thus, purely by way of example, the fan blade may have a carbon-fibre or aluminium based body (such as an aluminium lithium alloy) with a titanium leading edge.

A fan as described and/or claimed herein may comprise a central portion, from which the fan blades may extend, for example in a radial direction. The fan blades may be attached to the central portion in any desired manner. For example, each fan blade may comprise a fixture which may engage a corresponding slot in the hub (or disc). Purely by way of example, such a fixture may be in the form of a dovetail that may slot into and/or engage a corresponding slot in the hub/disc in order to fix the fan blade to the hub/disc. By way of further example, the fan blades maybe formed integrally with a central portion. Such an arrangement may be referred to as a bladed disc or a bladed ring.

Any suitable method may be used to manufacture such a bladed disc or bladed ring. For example, at least a part of the fan blades may be machined from a block and/or at least part of the fan blades may be attached to the hub/disc by welding, such as linear friction welding.

The gas turbine engines described and/or claimed herein may or may not be provided with a variable area nozzle (VAN). Such a variable area nozzle may allow the exit area of the bypass duct to be varied in use. The general principles of the present disclosure may apply to engines with or without a VAN.

The fan of a gas turbine as described and/or claimed herein may have any desired number of fan blades, for example 14, 16, 18, 20, 22, 24 or 26 fan blades.

As used herein, cruise conditions have the conventional meaning and would be readily understood by the skilled person. Thus, for a given gas turbine engine for an aircraft, the skilled person would immediately recognise cruise conditions to mean the operating point of the engine at mid-cruise of a given mission (which may be referred to in the industry as the "economic mission") of an aircraft to which the gas turbine engine is designed to be attached. In this regard, mid-cruise is the point in an aircraft flight cycle at which 50% of the total fuel that is burned between top of climb and start of descent has been burned (which may be approximated by the midpoint—in terms of time and/or distance—between top of climb and start of descent. Cruise conditions thus define an operating point of, the gas turbine engine that provides a thrust that would ensure steady state operation (i.e. maintaining a constant altitude and constant Mach Number) at mid-cruise of an aircraft to which it is designed to be attached, taking into account the number of engines provided to that aircraft. For example, where an engine is designed to be attached to an aircraft that has two engines of the same type, at cruise conditions the engine provides half of the total thrust that would be required for steady state operation of that aircraft at mid-cruise.

In other words, for a given gas turbine engine for an aircraft, cruise conditions are defined as the operating point of the engine that provides a specified thrust (required to provide—in combination with any other engines on the aircraft—steady state operation of the aircraft to which it is designed to be attached at a given mid-cruise Mach Number) at the mid-cruise atmospheric conditions (defined by the International Standard Atmosphere according to ISO 2533 at the mid-cruise altitude). For any given gas turbine engine for an aircraft, the mid-cruise thrust, atmospheric conditions and Mach Number are known, and thus the operating point of the engine at cruise conditions is clearly defined.

Purely by way of example, the forward speed at the cruise condition may be any point in the range of from Mach 0.7 to 0.9, for example 0.75 to 0.85, for example 0.76 to 0.84, for example 0.77 to 0.83, for example 0.78 to 0.82, for example 0.79 to 0.81, for example on the order of Mach 0.8, on the order of Mach 0.85 or in the range of from 0.8 to 0.85. Any single speed within these ranges may be part of the cruise condition. For some aircraft, the cruise conditions may be outside these ranges, for example below Mach 0.7 or above Mach 0.9.

Purely by way of example, the cruise conditions may correspond to standard atmospheric conditions (according to the International Standard Atmosphere, ISA) at an altitude that is in the range of from 10000 m to 15000 m, for example in the range of from 10000 m to 12000 m, for example in the range of from 10400 m to 11600 m (around 38000 ft), for example in the range of from 10500 m to 11500 m, for example in the range of from 10600 m to 11400 m, for example in the range of from 10700 m (around 35000 ft) to 11300 m, for example in the range of from 10800 m to 11200 m, for example in the range of from 10900 m to 11100 m, for example on the order of 11000 m. The cruise conditions may correspond to standard atmospheric conditions at any given altitude in these ranges.

Purely by way of example, the cruise conditions may correspond to an operating point of the engine that provides a known required thrust level (for example a value in the range of from 30 kN to 35 kN) at a forward Mach number of 0.8 and standard atmospheric conditions (according to the International Standard Atmosphere) at an altitude of 38000 ft (11582 m). Purely by way of further example, the cruise conditions may correspond to an operating point of the engine that provides a known required thrust level (for example a value in the range of from 50 kN to 65 kN) at a forward Mach number of 0.85 and standard atmospheric conditions (according to the International Standard Atmosphere) at an altitude of 35000 ft (10668 m).

In use, a gas turbine engine described and/or claimed herein may operate at the cruise conditions defined elsewhere herein. Such cruise conditions may be determined by the cruise conditions (for example the mid-cruise conditions) of an aircraft to which at least one (for example 2 or 4) gas turbine engine may be mounted in order to provide propulsive thrust.

According to an aspect, there is provided an aircraft comprising a gas turbine engine as described and/or claimed herein. The aircraft according to this aspect is the aircraft for which the gas turbine engine has been designed to be attached. Accordingly, the cruise conditions according to this aspect correspond to the mid-cruise of the aircraft, as defined elsewhere herein.

According to an aspect, there is provided a method of operating a gas turbine engine as described and/or claimed herein. The operation may be at the cruise conditions as defined elsewhere herein (for example in terms of the thrust, atmospheric conditions and Mach Number).

According to an aspect, there is provided a method of operating an aircraft comprising a gas turbine engine as described and/or claimed herein. The operation according to this aspect may include (or may be) operation at the mid-cruise of the aircraft, as defined elsewhere herein.

The skilled person will appreciate that except where mutually exclusive, a feature or parameter described in relation to any one of the above aspects may be applied to any other aspect. Furthermore, except where mutually exclusive, any feature or parameter described herein may be applied to any aspect and/or combined with any other feature or parameter described herein.

DESCRIPTION OF THE DRAWINGS

Embodiments will now be described by way of example only, with reference to the Figures, in which.

DETAILED DESCRIPTION

Aspects and embodiments of the present disclosure will now be discussed with reference to the accompanying figures. Further aspects and embodiments will be apparent to those skilled in the art.

Figure 1:
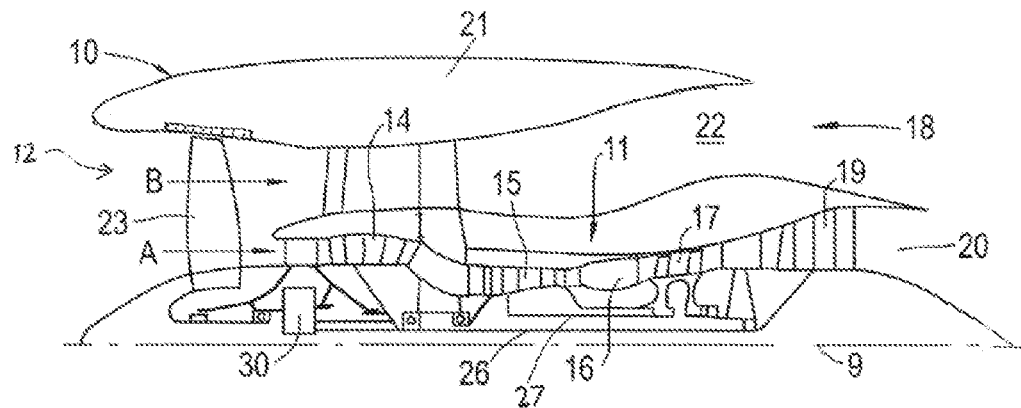
FIG. 1 is a sectional side view of a gas turbine engine.

FIG. 1 illustrates a gas turbine engine 10 having a principal rotational axis 9. The engine 10 comprises an air intake 12 and a propulsive fan 23 that generates two airflows: a core airflow A and a bypass airflow B. The gas turbine engine 10 comprises a core 11 that receives the core airflow A. The engine core 11 comprises, in axial flow series, a low pressure compressor 14, a high-pressure compressor 15, combustion equipment 16, a high-pressure turbine 17, a low pressure turbine 19 and a core exhaust nozzle 20. A nacelle 21 surrounds the gas turbine engine 10 and defines a bypass duct 22 and a bypass exhaust nozzle 18. The bypass airflow B flows through the bypass duct 22. The fan 23 is attached to and driven by the low pressure turbine 19 via a shaft 26 and an epicyclic gearbox 30.

In use, the core airflow A is accelerated and compressed by the low pressure compressor 14 and directed into the high pressure compressor 15 where further compression takes place. The compressed air exhausted from the high pressure compressor 15 is directed into the combustion equipment 16 where it is mixed with fuel and the mixture is combusted. The resultant hot combustion products then expand through, and thereby drive, the high pressure and low pressure turbines 17, 19 before being exhausted through the core exhaust nozzle 20 to provide some propulsive thrust. The high pressure turbine 17 drives the high pressure compressor 15 by a suitable interconnecting shaft 27. The fan 23 generally provides the majority of the propulsive thrust. The epicyclic gearbox 30 is a reduction gearbox.

Figure 2:
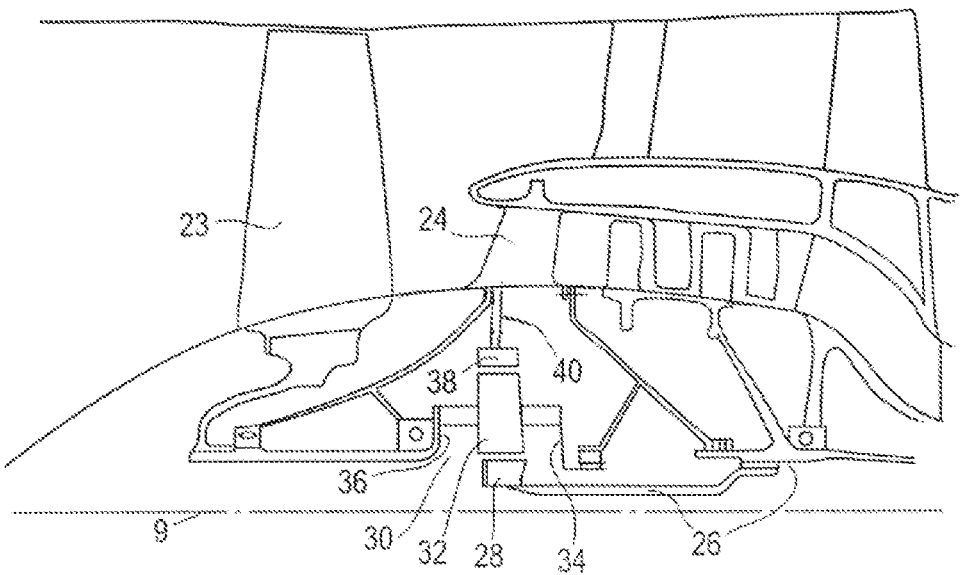
FIG. 2 is a close up sectional side view of an upstream portion of a gas turbine engine.

An exemplary arrangement for a geared fan gas turbine engine 10 is shown in FIG. 2. The low pressure turbine 19 (see FIG. 1) drives the shaft 26, which is coupled to a sun wheel, or sun gear, 28 of the epicyclic gear arrangement 30. Radially outwardly of the sun gear 28 and intermeshing therewith is a plurality of planet gears 32 that are coupled together by a planet carrier 34. The planet carrier 34 constrains the planet gears 32 to process around the sun gear 28 in synchronicity whilst enabling each planet gear 32 to rotate about its own axis. The planet carrier 34 is coupled via linkages 36 to the fan 23 in order to drive its rotation about the engine axis 9. Radially outwardly of the planet gears 32 and intermeshing therewith is an annulus or ring gear 38 that is coupled, via linkages 40, to a stationary supporting structure 24.

that the terms "low pressure turbine" and "low pressure compressor" as used herein may be taken to mean the lowest pressure turbine stages and lowest pressure compressor stages (i.e. not including the fan 23) respectively and/or the turbine and compressor stages that are connected together by the interconnecting shaft 26 with the lowest rotational speed in the engine (i.e. not including the gearbox output shaft that drives the fan 23). In some literature, the "low pressure turbine" and "low pressure compressor" referred to herein may alternatively be known as the "intermediate pressure turbine" and "intermediate pressure compressor". Where such alternative nomenclature is used, the fan 23 may be referred to as a first, or lowest pressure, compression stage.

Figure 3:
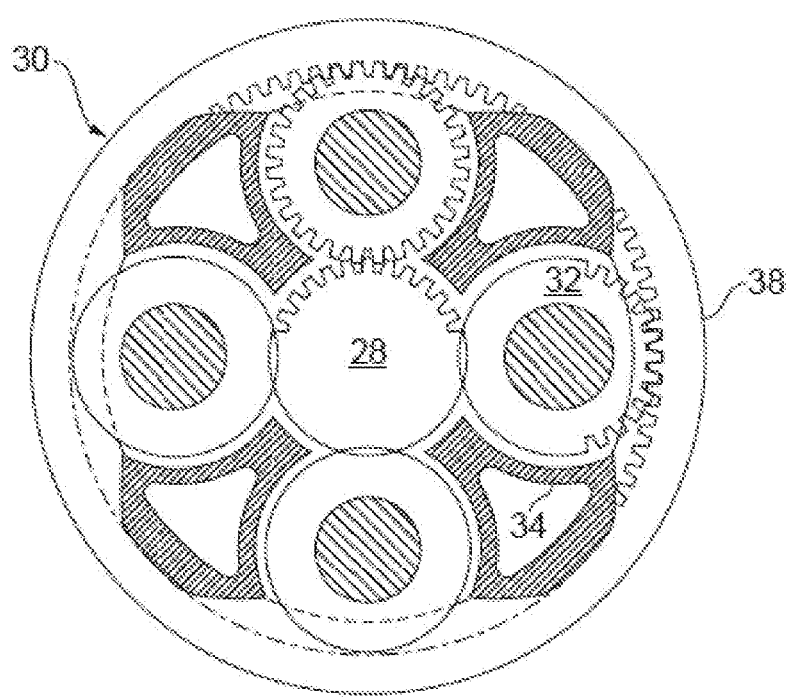
FIG. 3 is a partially cut-away view of a gearbox for a gas turbine engine.

The epicyclic gearbox 30 is shown by way of example in greater detail in FIG. 3. Each of the sun gear 28, planet gears 32 and ring gear 38 comprise teeth about their periphery to intermesh with the other gears. However, for clarity only exemplary portions of the teeth are illustrated in FIG. 3. There are four planet gears 32 illustrated, although it will be apparent to the skilled reader that more or fewer planet gears 32 may be provided within the scope of the claimed invention. Practical applications of a planetary epicyclic gearbox 30 generally comprise at least three planet gears 32.

The epicyclic gearbox 30 illustrated by way of example in FIGS. 2 and 3 is of the planetary type, in that the planet carrier 34 is coupled to an output shaft via linkages 36, with the ring gear 38 fixed. However, any other suitable type of epicyclic gearbox 30 may be used. By way of further example, the epicyclic gearbox 30 may be a star arrangement, in which the planet carrier 34 is held fixed, with the ring (or annulus) gear 38 allowed to rotate. In such an arrangement the fan 23 is driven by the ring gear 38. By way of further alternative example, the gearbox 30 may be a differential gearbox in which the ring gear 38 and the planet carrier 34 are both allowed to rotate.

It will be appreciated that the arrangement shown in FIGS. 2 and 3 is by way of example only, and various alternatives are within the scope of the present disclosure. Purely by way of example, any suitable arrangement may be used for locating the gearbox 30 in the engine 10 and/or for connecting the gearbox 30 to the engine 10. By way of further example, the connections (such as the linkages 36, 40 in the FIG. 2 example) between the gearbox 30 and other parts of the engine 10 (such as the input shaft 26, the output shaft and the fixed structure 24) may have any desired degree of stiffness or flexibility. By way of further example, any suitable arrangement of the bearings between rotating and stationary parts of the engine (for example between the input and output shafts from the gearbox and the fixed structures, such as the gearbox casing) may be used, and the disclosure is not limited to the exemplary arrangement of FIG. 2. For example, where the gearbox 30 has a star arrangement (described above), the skilled person would readily understand that the arrangement of output and support linkages and bearing locations would typically be different to that shown by way of example in FIG. 2.

Accordingly, the present disclosure extends to a gas turbine engine having any arrangement of gearbox styles (for example star or planetary), support structures, input and output shaft arrangement, and bearing locations.

Optionally, the gearbox may drive additional and/or alternative components (e.g. the intermediate pressure compressor and/or a booster compressor).

Other gas turbine engines to which the present disclosure may be applied may have alternative configurations. For example, such engines may have an alternative number of compressors and/or turbines and/or an alternative number of interconnecting shafts. By way of further example, the gas turbine engine shown in FIG. 1 has a split flow nozzle 18, 20 meaning that the flow through the bypass duct 22 has its own nozzle 18 that is separate to and radially outside the core exhaust nozzle 20. However, this is not limiting, and any aspect of the present disclosure may also apply to engines in which the flow through the bypass duct 22 and the flow through the core 11 are mixed, or combined, before (or upstream of) a single nozzle, which may be referred to as a mixed flow nozzle. One or both nozzles (whether mixed or split flow) may have a fixed or variable area. Whilst the described example relates to a turbofan engine, the disclosure may apply, for example, to any type of gas turbine engine, such as an open rotor (in which the fan stage is not surrounded by a nacelle) or turboprop engine, for example. In some arrangements, the gas turbine engine 10 may not comprise a gearbox 30.

The geometry of the gas turbine engine 10, and components thereof, is defined by a conventional axis system, comprising an axial direction (which is aligned with the rotational axis 9), a radial direction (in the bottom-to-top direction in FIG. 1), and a circumferential direction (perpendicular to the page in the FIG. 1 view). The axial, radial and circumferential directions are mutually perpendicular.

Figure 4:
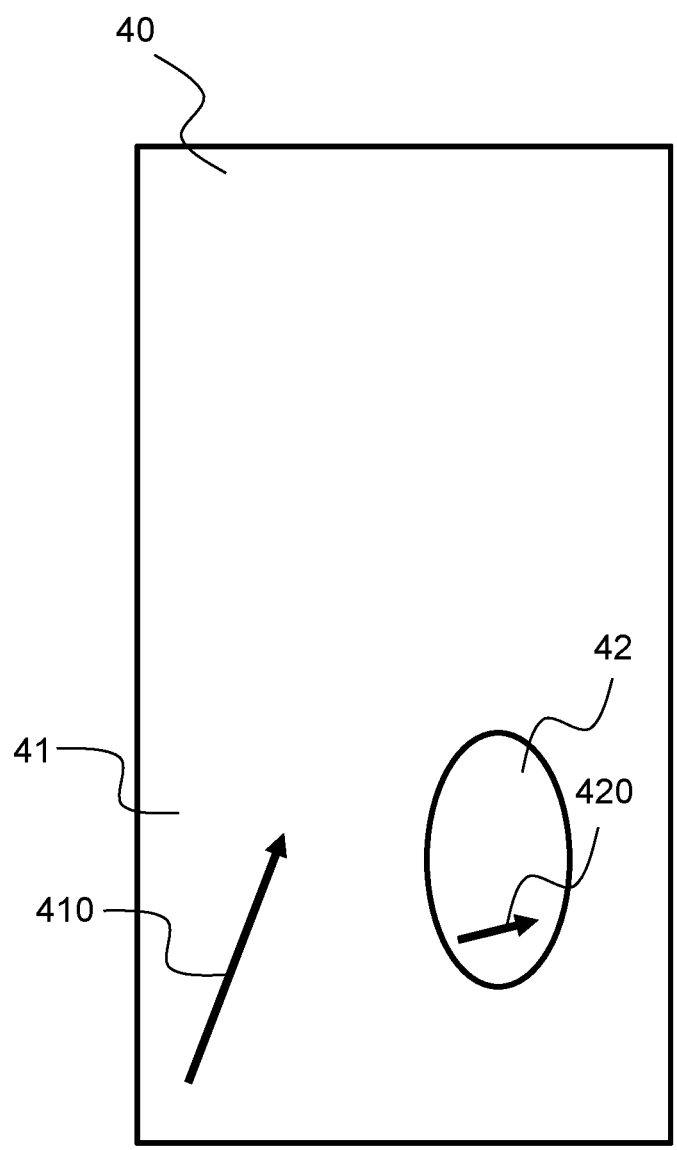
FIG. 4 is a schematic example of a component comprising two different crystal grains.

FIG. 4 shows a schematic example of a component 40 that may present inside a gas turbine engine 10 as discussed above. The component may be a turbine blade of the gas turbine engine 10.

The component 40 may be formed from a metal alloy, for example nickel, and the manufacturing process for the component 40 may be intended to result in a single crystal alloy. The component 40 may comprise a first crystal grain region 41. The first crystal grain may be the intended crystal grain from which the component 40 is to be formed. The first crystal grain region 41 has a particular crystal grain axis 410.

If the manufacturing process for the component 40 has been performed successfully, the first crystal grain region 41 may be the only crystal grain present in the component 40. Alternatively, a second crystal grain region 42 may also be present in the component 40. The second crystal grain region 42 has a crystal grain axis 420 that is different to the crystal grain axis 410 of the first crystal grain region 41.

The presence of the second crystal grain region 42 may be considered a defect. The presence of the defect may be due to an error in the manufacturing process of the component 40. Alternatively, the presence of defects may be unavoidable but it may be desirable to reduce the presence of defects in the component 40.

It is possible to obtain information about the presence of such defects through optical analysis of the surface of the component. For example, when a component 40 formed of a nickel material is cast and goes through a blast and etch process, gamma prime precipitate blocks form the optical surface of the component. The presence of a second crystal grain 42 at the surface of the component 40 may cause a change in behaviour of light illuminating the component 40. For example, the difference in the angle of the crystal grain axis 420 of the second crystal grain region 42 to the crystal grain axis 410 of the first crystal grain region 41 (known as the sheer angle) may cause a shift in the angular position of maximum reflectance from the surface of the component 40.

The gamma prime precipitate blocks which form the surface of the component 40 may have a similar size distribution to the wavelength of light used to illuminate the surface. In this case, the surface of the component 40 may exhibit diffraction grating like properties. The presence of a second crystal grain region 42 at a different crystal grain axis 420 results in an in-plain rotation of the diffraction grating like surface, which causes a polarisation shift in light reflected from the surface. Therefore, the presence of a second crystal grain region 42 may cause a change in the polarisation angle of light illuminating the surface of the component 40 when compared to light illuminating the first crystal grain region 41.

It is therefore possible to obtain information about the presence of a second crystal grain region 42 within a component 40 by imaging the component 40 using different polarisations states of light. It is also possible to obtain information about the presence of a second crystal grain region 42 by imaging the component 40 using a single polarisation state of light by comparing the polarisation state of different regions of an obtained image of the component 40.

Figure 5:
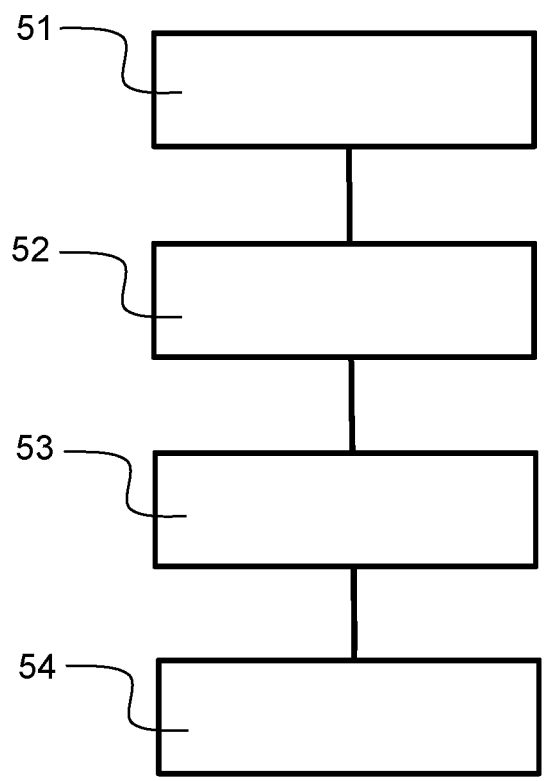
FIG. 5 is a flow chart indicating the steps in the method of the present application.

An example of the steps of such a method is shown in FIG. 5. In a first step 51, a first image of the component 40 is obtained. To obtain the first image, the component 40 is illuminated with light of a first polarisation state and a first image of the component 40 is recorded by a detector array comprising a plurality of pixels, where the first image includes polarisation data such as the polarisation angle recorded for each pixel.

In a second step 52, a second image of the component 40 may be obtained. When obtaining the second image, the component 40 is illuminated using light of a second polarisation state which is different to the first polarisation state. The second image also includes polarisation data such as the polarisation angle recorded for each pixel.

The method described above may be performed with various different polarisation states. For example, both the first polarisation state used to obtain the first image and the second polarisation state used to obtain the second image may be linear polarisation states. In this case, the polarisation angle of the first state may be different to the second state. Alternatively, one of the states may be a circular polarisation state. Different polarisation states may be used depending on the nature of the defect and the component being analysed.

In a third step 53, a difference in polarisation is be calculated. If only the first image of the component 40 has been obtained, the difference in polarisation may be determined between different regions of the first image. For example, each pixel of the first image may be compared to at least one other pixel of the first image. In the case where the second image has been obtained, the first image of the component 40 and the second image of the component 40 are compared. A plurality of pixels in the first image may be compared to corresponding pixels of the second image. Corresponding pixels may be pixels from each image that represent the same point on the surface of the component 40.

A difference in the measured polarisation between corresponding pixels may be calculated. For example, the change in the recorded polarisation angle between the corresponding pixels may be calculated.

In a fourth step 54, pixels corresponding to the second crystal grain region 42 may be determined based on the calculated difference in polarisation. Using this method, regions of the second crystal grain region 42, which may be a defect in the component 40 as discussed above, can be identified. Identification of various properties of such defect regions may allow selection of components with minimal or no defects. Identification of the properties may allow improvement of the manufacturing method of the component 40 by comparing the properties defects between different components manufactured using different methods.

The different regions in the component 40 may be identified in different ways. For example, particular regions of the component 40 may be characterised as being part of the first region 41 if the calculated polarisation difference falls into a first range. Particular regions of the component 40 may be characterised as being part of the second region 42 if the calculated polarisation difference falls into a second range. Alternatively, a region of the image may be categorised as being part of the second region 42 if the calculated in polarisation exceeds a threshold value.

The calculated difference in polarisation may be used to determine further information about the second crystal grain region 42. For example, the calculated difference in polarisation may be used to calculate the angle of orientation of the second crystal grain axis 420 relative to the angle of orientation of the first crystal grain axis 410. The boundary between the two regions may also be determined. The area of the second crystal grain region 42, either as an absolute value or relative to the area of the first crystal grain region 41 may also be obtained.

Each of the first image and the second image may be obtained with at least one of the illumination source and the light receiver arranged at the same orientation relative to the component 40. In this case, identifying corresponding pixels in the first and the second images may be simpler as corresponding pixels will be at the same location in each image.

Additional information may be used to assist with the identification of the second crystal grain region 42. For example, when the polarisation information of the first image and the second image is obtained, intensity data may also be obtained for each pixel. A difference in intensity between different pixels within the first image or corresponding pixels of the first image and the second image may be calculated. The calculated difference in intensity may be used in addition to the calculated difference in polarisation when determining the properties of the second crystal grain region 42 as discussed above.

The method discussed above is not limited to the obtaining of only two images. Any number of images may be obtained, where each of the further plurality of images is obtained using a different polarisation state of light to each of the other plurality of images. For example, a plurality of images may be obtained, where linearly polarised light is used to illuminate the object 40 and the polarisation angle of the light is stepped through in each subsequent image. When a plurality of images has been obtained, the polarisation values of each of the pixels of the plurality of images may be stored as a matrix of image data. Identification of pixels corresponding to the second crystal grain region 42 may be performed by analysis of the matrix of image data. Data mining and deep learning techniques such as the analysis of the matrix of image data using trained neural networks may be used.

Figure 6:
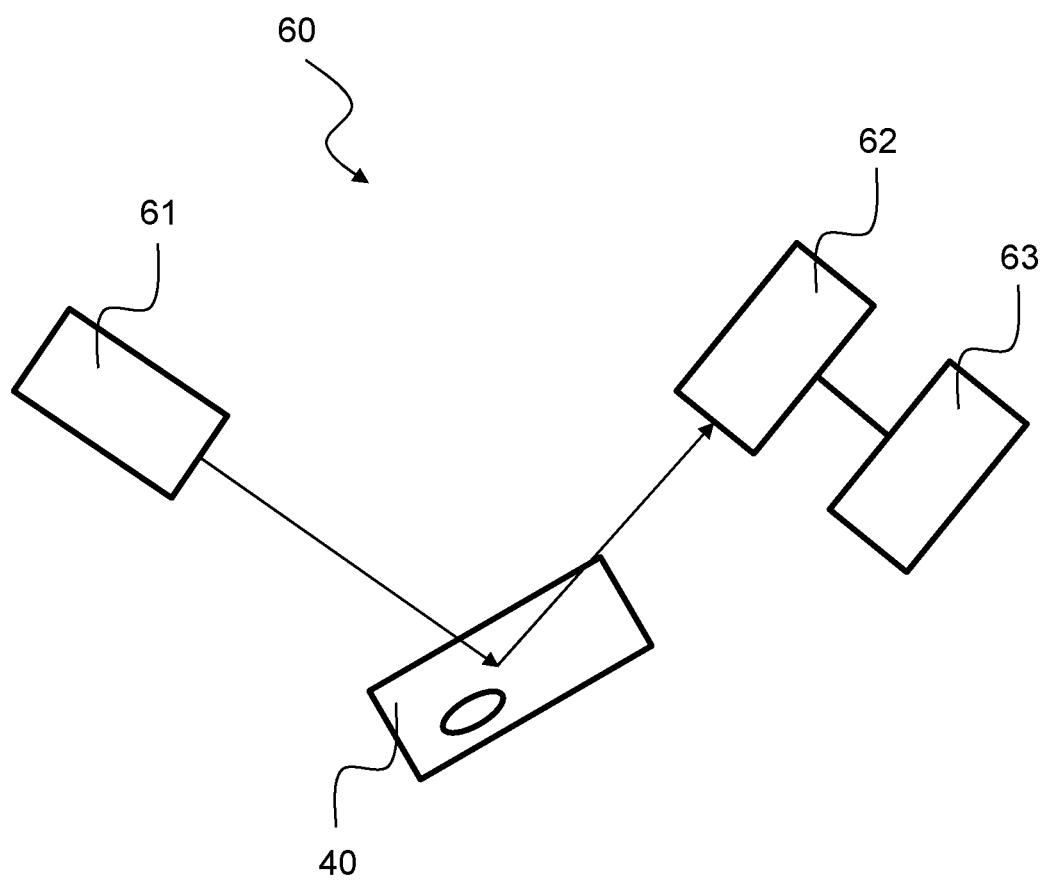
FIG. 6 is a schematic illustration of apparatus used to perform polarisation imaging.

FIG. 6 shows a schematic example of apparatus 60 which may be used to perform the method discussed above. A light source 61 is used to illuminate the component 40 in a plane of incidence. The light source 61 may be capable of producing polarised light in various polarisation states, such as linear polarisation states at different angles and circular polarisation states as discussed above.

The light reaches the component 40, is reflected in the plane of incidence and is received by a detector 62. The detector 62 may comprise a sensor with multiple pixels, where in each pixel is configured to detect the polarisation state of light incident on the pixel. Image data obtained by the detector 62 may be passed to an analyser 63. The analyser 63 may compare the image data of multiple images obtained by the detector 62 to calculate the differences in polarisation as discussed above.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

I claim:

1. A method of analysing a component formed from a metal alloy to identify a possible defect, wherein the metal alloy comprises a first crystal grain region and the possible defect comprises a second crystal grain region aligned to a different axis to the first crystal grain region, the method comprising the steps of:
   obtaining a first image of the component using a multi-pixel sensor and illuminated using a first polarisation state of light, the first image comprising first polarisation data across a plurality of pixels within the multi-pixel sensor;
   obtaining a second image of the component using a multi-pixel sensor and illuminated using a second polarisation state of light different to the first polarisation state, the second image comprising second polarisation data across a plurality of pixels within the multi-pixel sensor;
   determining a difference between the first and second polarisation data for the plurality of pixels of the first image and a corresponding plurality of pixels of the second image; and
   identifying pixels corresponding to the second crystal grain region based on the difference in first polarisation data from the plurality of pixels of the first image and second polarisation data of the corresponding plurality of pixels of the second image.

2. The method of claim 1, wherein a pixel is categorised as corresponding to the first crystal grain region if the difference between first polarisation data from the plurality of pixels of the first image and second polarisation data of the corresponding plurality of pixels of the second image falls within a first range, or corresponding to the second crystal grain region if the difference between first polarisation data from the plurality of pixels of the first image and second polarisation data of the corresponding plurality of pixels of the second image falls within a second range, where the first range is different to the second range.

3. The method of claim 1, wherein a pixel is categorised as corresponding to the second crystal grain region if the difference in first and second polarisation data exceeds a threshold value.

4. The method of claim 1, further comprising determining the angle of orientation of the second crystal grain region relative to the angle of orientation of the first crystal grain region based on the difference in first and second polarisation data.

5. The method of claim 1, further comprising determining the location of the boundary between the second crystal grain region and the first crystal grain region based on the difference in first and second polarisation data.

6. The method of claim 1, further comprising determining the area of the second crystal grain region based on the difference in first and second polarisation data.

7. The method of claim 1, wherein the component is illuminated using the first polarisation state of light at the same perspective and orientation relative to the illumination using the second polarisation stage of light.

8. The method of claim 1, wherein the second image is obtained at the same perspective and orientation relative to the component as the first image.

9. The method of claim 1, wherein at least one of the first and second polarisation states is a circular polarisation state.

10. The method of claim 1, wherein each of the first image and the second image further comprise intensity data; and
   the method further comprises the step of determining a difference in intensity for plural pixels of the first image between each pixel of the first image and a corresponding pixel of the second image;
   wherein the identification of pixels corresponding to the second crystal grain region is additionally based on the difference in intensity.

11. The method of claim 1, further comprising obtaining a plurality of further images of the component, wherein each of the further plurality of images is obtained using a different polarisation state to each of the other of the further plurality of images; and storing the polarisation data of each of the images of the component in a matrix of image data;

wherein the identification of pixels corresponding to the second crystal grain region is performed by analysis of the matrix of image data.

12. The method of claim 1, wherein at least one of the first and second polarisation states of light is a linear polarisation state.

13. The method of claim 12, wherein both of the first and second polarisation states of light are linear polarisation states and incident upon the component in a plane of incidence, the first linear polarisation state being at a different polarisation angle with respect to the plane of incidence to the second linear polarisation state.

14. An apparatus for analysing a component formed from a metal alloy, the apparatus comprising:

a light source configured to produce polarised light;

a detector comprising a sensor with multiple pixels, each pixel configured to detect the polarisation state of light incident on the pixel; and an analyser;

wherein the apparatus is configured to perform the method of claim 1.

15. A method of analysing a component formed from a metal alloy to identify a possible defect, wherein the metal alloy comprises a first crystal grain region and the possible defect comprises a second crystal grain region aligned to a different axis to the first crystal grain region; and the method comprises the steps of:

obtaining an image of the component illuminated using a first polarisation state of light, the first image comprising polarisation data;

determining a difference in polarisation data for plural pixels of the first image between each pixel of the first image and at least one other pixel of the first image; and identifying pixels corresponding to the second crystal grain region based on the difference in polarisation data.

16. The method of claim 15, wherein each pixel is categorised as corresponding to the first crystal grain region by identifying a first region of the differences in polarisation data in a first range or corresponding to the second crystal grain region by identifying a second region of the differences in polarisation data in a second range, where the first range is different to the second range.

17. The method of claim 15, wherein each pixel is categorised as corresponding to the second crystal grain region if the difference in polarisation data exceeds a threshold value.

18. The method of claim 15, further comprising determining the angle of orientation of the second crystal grain region relative to the angle of orientation of the first crystal grain region based on the difference in polarisation data.

19. The method of claim 15, further comprising determining the location of the boundary between the second crystal grain region and the first crystal grain region based on the difference in polarisation data.

20. The method of claim 15, further comprising determining the area of the second crystal grain region based on the difference in polarisation data.

* * * * *